United States Patent [19]

Bettinger

[11] Patent Number: 5,368,588
[45] Date of Patent: * Nov. 29, 1994

[54] PARENTERAL FLUID MEDICATION RESERVOIR PUMP

[76] Inventor: David S. Bettinger, 8030 Coventry, Grosse Ile, Mich. 48138

[ * ] Notice: The portion of the term of this patent subsequent to Feb. 23, 2010 has been disclaimed.

[21] Appl. No.: 23,130

[22] Filed: Feb. 26, 1993

[51] Int. Cl.$^5$ ............................................. A61K 9/22
[52] U.S. Cl. .............................. 604/891.1; 604/131; 604/132; 424/423; 222/386.5
[58] Field of Search .................. 604/132, 131, 892.1, 604/891.1, 890.1; 424/420, 421, 423, 424, 425; 222/386.5

[56] References Cited

U.S. PATENT DOCUMENTS

| | | | |
|---|---|---|---|
| 3,710,795 | 1/1973 | Higuchi et al. | 128/833 |
| 4,180,073 | 12/1979 | Michaels | 604/892.1 |
| 4,192,308 | 3/1980 | Michaels | 604/892.1 |
| 4,304,232 | 12/1981 | Michaels | 604/892.1 |
| 4,957,119 | 9/1990 | de Nijs | 604/890.1 |
| 5,019,372 | 5/1991 | Folkman et al. | 604/891.1 |
| 5,053,032 | 10/1991 | Barclay et al. | 604/892.1 |
| 5,188,260 | 2/1993 | Bettinger | 222/107 |

Primary Examiner—John G. Weiss

[57] ABSTRACT

A parenteral fluid medication pump comprises a reservoir filled with fluid medication. The medication is continuously discharged over an extended period into the patient. The continuous discharge is obtained by a shrink polymer wall for the reservoir which is powered by the relaxation of forces which are internal to the shrink polymer. In the principal embodiment the device pumps from a reservoir which is surgically implanted and internal to the patient. A reservoir depletion warning for surgically implanted pumps which creates a physiological indicator is also taught. In other embodiments the device is capable of magnetic, external-triggered disablement.

7 Claims, 2 Drawing Sheets

– 1 –

PARENTERAL FLUID MEDICATION RESERVOIR PUMP

CROSS-REFERENCES TO RELATED APPLICATIONS

07/709,219 Jun. 3, 1991 Betringer Art Unit 3108 DEROSA U.S. Pat. No. 5,188,260 Feb. 23, 1993.

STATEMENT AS TO RIGHTS TO INVENTIONS MADE UNDER FEDERALLY-SPONSORED RESEARCH AND DEVELOPMENT

No Federally-sponsored work was associated with this invention.

BACKGROUND OF THE INVENTION

1. Field of Invention

This invention generally relates to a pump for dispensing parenteral fluid medication and more particularly to a pump which is surgically implanted to administer such medications by the induced flow of an internal reservoir over an extended period of time. In such implant devices find usage for the ambulatory patient requiring an extended regimen such as for a chronic condition or for birth control. About half of all ethical pharmaceuticals are consumed for a chronic condition. Such implant devices also find usage for the acute patient in transit where neither an IV gravity bag, nor continuous injections can be used.

2. Description of the Prior Art

Prior art on continuous medication where the reservoir is external to the patient includes
gravity feed,
power-driven pumps,
elastic bladder pumps,
gas pressurized pumps. For an acute patient in transit, gravity IV may be cumbersome, power may be unavailable, or the duration of elastic bladders and gas pressure pumps may be too short.

Prior art on continuous medication where the reservoir is internal to the patient as an indwelling implant includes
osmotic powered pumps,
exuding or diffusion controlled polymers,
eroding systems, and
power-driven pumps. Osmotic implant durations are limited to 30 days. Exuding implants have durations of up to five years, but have decreasing sloped delivery curves as shown in the 1992 *Physicians' Desk Reference*, page 2484. Eroding implants are difficult to develop because the drug, the vehicle, and the binder must all be compatible, and predictably benign when absorbed. Power-driven pump implants are complex and expensive.

SUMMARY OF THE INVENTION

1. Objects of the Invention

It is a general object of this invention to overcome the aforementioned drawbacks of prior art medication dispensing systems. It is another general object of this invention to teach the continuous dispensing of medication by shrink polymer pumps. It is another object of this invention to dispense fluid medication at a reliable, flat delivery rate. It is a further object of this invention to provide an inexpensive pump which takes up little volume of space because the package is the pump. It is another object of this invention to provide a universal Infuser implant pump for all intravenous, intramuscular, or subcutaneous extended-regimen drugs including hormones, cardiovascular, antibiotics, and psychotropics. It is still another object of this invention to provide a pump capable of programmable multi-drug sequencing. It is yet another object of this invention to provide a safe drug dispenser with safeguards for patient self-monitoring and pump disablement.

2. Features of the Invention

In keeping with these objects and others which will become apparent hereinafter, one feature of this invention resides, briefly stated, in a disposable parenteral fluid medication pump comprising an elongated reservoir having an enclosing wall; said reservoir having at least one closable outlet through which a flowable fluid is induced to administer a medication; and wherein said reservoir wall is made of shrink polymer material which when activated results in a reduction in the interior volume of said reservoir forcing said flowable fluid through said outlet; and wherein said shrink polymer material is activated by heat, aging, light, chemical agent, oxygen, or a combination. Such shrink polymers are well known and their use in general dispensing is taught by Bettinger in U.S. Pat. No. 5,188,260.

In accordance the preferred embodiment of this invention as an implant pump wherein the bio-compatible polymer pump is surgically implanted for such periods as may be required for the medication or medications resident in the charge with the duration of the implantation achieved by the age activated shrink-polymers selected. For example, poor patient compliance with oral medication during the treatment of tuberculosis leads to drug resistance and contagion. A 60 day duration implant dispensing antibiotics by age-shrinkage would be a major step toward regaining control of the disease. Because most shrink polymers are temperature responsive, the fixed ambient temperature of the patient's body provides a flat delivery curve.

It will be understood by one skilled in the art that said pump implant may be prepared with one end drawn to a point to facilitate insertion in flesh and which by shape memory achieves after implantation a more rounded and thereby less irritating shape.

It will also be understood by one skilled in the art that said implant pump may be coated with polymers which enhance bio-compatability.

It will also be understood by one skilled in the art that the dispensing status of such a subcutaneous semi-transparent implant can be visually monitored by the use of dye for all or a portion of the charge together with the proper external application of a light of selected strength and spectrum to penetrate the skin and make visible the dye.

In accordance with a second embodiment of this invention wherein the reservoir of said implant pump is charged by the insertion of a prefilled flexible tube, bag, sack, or pouch containing the fluid to be administered. The shrink-polymer implant pump may thus be stored separately awaiting application and activation.

In accordance with a third embodiment of this invention, when during administration said shrink polymer pump is activated by the patients body temperature then insulation means are provided for maintaining a uniform temperature at the reservoir site by shielding said pump from temperature variations.

In accordance with a fourth embodiment of this invention, wherein the reservoir outlet is mounted in communication with a means for continuous administering medication such as a hollow tube for site targeting or multi-drug sequencing. For site targeting a subcutaneous site allows status monitoring with said hollow tube dispensing end placed directly within a tumor. For multi-drug sequencing, drugs may be arranged in linear array within either said hollow tube or said pump of small diameter and programmed by concentration, and amount to satisfy a complex regimen of months or years.

In accordance with a fifth embodiment of this invention, wherein said pump has a magnetic, externally activated, disabling device. It will be understood by one skilled in the art that a hypodermic can be used to pierce the skin and the pump wall to withdraw a portion of the charge to also forestall short-term dispensing.

In accordance with a sixth embodiment of this invention, wherein said pump which achieves in its post-dispensing state, a relaxed shape in which the opposing internal surfaces are adjacent and parallel, so as to minimize any residual undispensed charge.

In accordance with an independent embodiment of this invention, any surgically implanted medication dispenser internal to the patient wherein at or near the exhaustion of the medication the implant dispenses a drug which creates a perceptible or observable physiological change in the patient as an indicator for medication exhaustion or implant removal.

For example the medication exhaustion indicator wherein the indicator drug is methylene blue would color the urine, alerting the patient to seek further medical care and implant removal.

DESCRIPTION OF THE PREFERRED EMBODIMENTS

Figure 1:
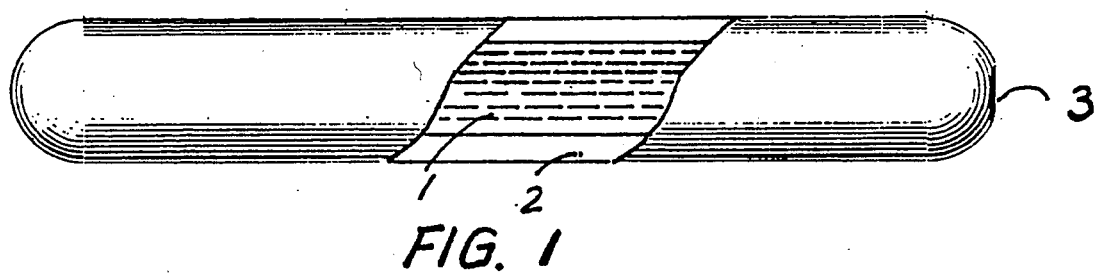
FIG. 1 is an elevation and partial section through an embodiment of a pump used as a surgical implant.

Referring now to the drawings, reference number 1 identifies a first embodiment pump in FIG. 1. As the pump shrinks it constricts the volume of the reservoir 2 thereby dispensing fluid 2 through the outlet at 3.

Figure 2:
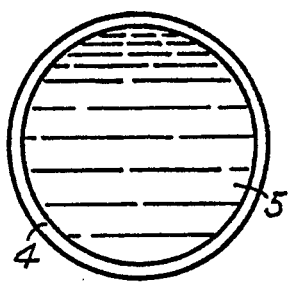
FIG. 2 is a transverse section through a pump prior to shrinkage dispensing.

In FIG. 2 the pump 4 in its unconstricted state when implanted takes the form in section of a cylinder containing a reservoir 5.

Figure 3:
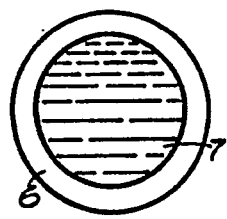
FIG. 3 through FIG. 5 are transverse sections through pumps after shrinkage dispensing which revert to shapes of varying dispensing efficiency.

In FIG. 3 the pump 6 is shown in a depleted state when final shape of the pump 6 has been determined to be a cylinder. In this case the cylindrical shape has shrunken radially. If the shrink polymer has had a 30% dimensional reduction, then the reservoir has retained about 50% of its charge as unused follower fluid.

Figure 4:
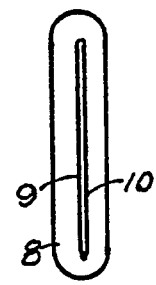

FIG. 4 shows an embodiment of the pump 8 which minimizes the reservoir volume at depletion by utilizing the shape memory of the polymer material at the two lobes to bring the two opposing faces 9 and 10 of the internal surface into parallel.

Figure 5:
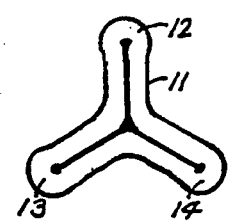

It will be understood by one skilled in the art that multiple lobes may follow the rule taught by this invention of bringing opposing faces into parallel. In FIG. 5 a three lobe pump 11 has dispensed its charge aided by the thickened ends of lobes 12, 13, 14 to increase the strength required of the shape memory polymer at the lobe ends 12.

Figure 6:
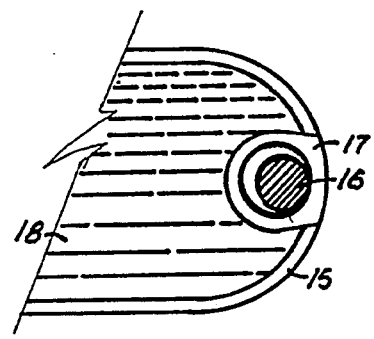
FIG. 6 is a section through the wall of a pump showing a disabling plug removable means.

In FIG. 6 the pump wall 15 has the outlet closed by a plug 17 with a magnetic core 16. Immediate short term cessation of drug dispensing is accomplished by applying a strong magnet to the implant to move and seat the plug 17.

Figure 7:
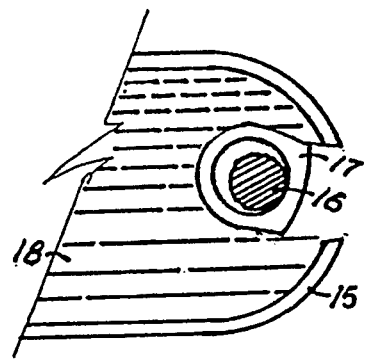
FIG. 7 is a longitudinal section through s pump showing the magnetic plug in a displaced position.

In FIG. 7 the plug 17 is moved and seated within pump 18 after an external magnet acts on the magnetic core 18 of the plug.

Figure 8:
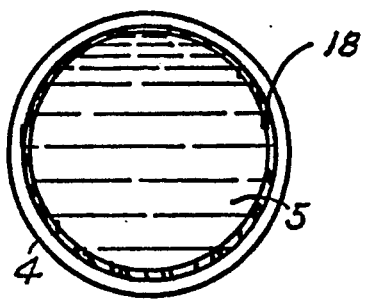
FIG. 8 is a transverse section through a pump prior to shrinkage dispensing showing the prefilled container for the charge.

In FIG. 8 the pump 5 is charged with a container 18, prefilled with medication prior to dispensing.

Figure 9:
FIG. 9 is a schematic showing a small diameter tube connected to the pump for multi-drug sequencing.

In FIG. 9 a small diameter hollow tube 20 is connected to pump 19 for multi-drug sequencing. The nonmisable medications are shown schematically as alternating charges in the tube 20.

Figure 10:
FIG. 10 is a schematic showing a small diameter pump for multi-drug sequencing.

In FIG. 10 the pump 21 is formed as a long, small-diameter, tubular, multi-drug sequencer. The non-misable medications are shown schematically as alternating charges in the pump 21.

What is claimed as new and desired to be protected by Letter Patent is set forth in the appended claims.

1. A disposable parenteral fluid medication pump comprising an elongated reservoir having an enclosing wall;
   said reservoir having at least one closable outlet through which a flowable fluid is induced to administer a medication; and
   wherein said wall is made of shrink polymer material which when activated results in a reduction in the interior volume of said reservoir forcing said flowable fluid through said outlet; and
   wherein said shrink polymer material is activated by heat, aging, light, chemical agent, oxygen, or a combination.

2. The pump of claim 1 wherein the pump is made of age activated, shrink polymers which are bio-compatible with surgical implantation in a patient for such periods as are required for complete dispensing of medication.

3. The pump of claim 1 wherein the reservoir outlet is mounted in communication with a means for continuous administering medication by attaching a hollow tube to said outlet for site-targeting and multi-drug sequencing.

4. The implant pump of claim 2 wherein said pump has a disabling device comprising a plug having a magnetic core.

5. The pump of claim 1 wherein the reservoir is charged by the insertion of a container, prefilled with the medication to be administered.

6. The pump of claim 1 wherein the opposing internal walls in the post dispensing state are adjacent and parallel to minimize residual undispensed charge.

7. A disposable parenteral fluid medication pump comprising an elongated reservoir of small diameter having an enclosing wall; said reservoir having at least one closable outlet through which a plurality of medications are induced in a linear sequence to achieve a preprogrammed regimen; and wherein said reservoir wall is made of shrink polymer material which when activated results in a reduction in the interior volume of said reservoir forcing said medications through said outlet; and wherein said shrink polymer material is activated by heat, aging, light, chemical agent, oxygen, or a combination.

* * * * *